(12) United States Patent
Beselt

(10) Patent No.: US 9,753,114 B2
(45) Date of Patent: Sep. 5, 2017

(54) GAP AND DISPLACEMENT MAGNETIC SENSOR SYSTEM FOR SCANNER HEADS IN PAPER MACHINES OR OTHER SYSTEMS

(71) Applicant: Honeywell ASCa Inc., Mississauga (CA)

(72) Inventor: Ronald E. Beselt, Burnaby (CA)

(73) Assignee: Honeywell Limited, Mississauga (CA)

( * ) Notice: Subject to any disclaimer, the term of this patent is extended or adjusted under 35 U.S.C. 154(b) by 375 days.

(21) Appl. No.: 14/579,978

(22) Filed: Dec. 22, 2014

(65) Prior Publication Data

US 2016/0123773 A1    May 5, 2016

Related U.S. Application Data

(60) Provisional application No. 62/074,186, filed on Nov. 3, 2014.

(51) Int. Cl.
| | |
|---|---|
| *G01R 35/00* | (2006.01) |
| *G01D 5/14* | (2006.01) |
| *G01N 33/34* | (2006.01) |
| *D21G 9/00* | (2006.01) |
| *G01B 7/14* | (2006.01) |

(52) U.S. Cl.
CPC ......... *G01R 35/005* (2013.01); *D21G 9/0009* (2013.01); *G01B 7/14* (2013.01); *G01D 5/147* (2013.01); *G01N 33/346* (2013.01)

(58) Field of Classification Search
None
See application file for complete search history.

(56) References Cited

U.S. PATENT DOCUMENTS

| | | | |
|---|---|---|---|
| 6,281,679 B1 * | 8/2001 | King | G01B 7/107 |
| | | | 324/226 |
| 2003/0066200 A1 | 4/2003 | Hellstrom | |
| 2005/0229420 A1 * | 10/2005 | Brenner | G01B 7/012 |
| | | | 33/558 |

(Continued)

FOREIGN PATENT DOCUMENTS

| | | |
|---|---|---|
| CA | 2097518 | 7/1992 |
| CA | 2356337 | 6/2000 |
| GB | 1576994 | 10/1980 |

OTHER PUBLICATIONS

International Search Report and Written Opinion issued for PCT/CA2015/000562 dated Jan. 13, 2016, 10 pgs.

*Primary Examiner* — Son Le
*Assistant Examiner* — Alvaro Fortich

(57) ABSTRACT

A gap and displacement magnetic sensor system for scanner heads in paper machines or other systems includes a multiple-sensor assembly. The multiple-sensor assembly includes multiple magnetic field orientation sensors configured to capture measurements of a magnetic field in order to identify (i) a displacement of first and second scanning sensor heads in a first direction, and (ii) a gap separation of the first and second scanning sensor heads in a second direction, and (iii) a displacement of the first and second scanning sensor heads in a third direction. At least one of the magnetic field orientation sensors is disposed offset from a centerline of the magnetic field such that an output from the at least one magnetic field orientation sensor indicates a combination of the gap separation and the displacement in either the first direction or the third direction.

20 Claims, 8 Drawing Sheets

(56) References Cited

U.S. PATENT DOCUMENTS

| | | | |
|---|---|---|---|
| 2006/0071818 A1* | 4/2006 | Muller | G01D 5/2497 |
| | | | 341/15 |
| 2006/0132808 A1* | 6/2006 | Jasinski | G01B 11/0691 |
| | | | 356/632 |
| 2007/0058212 A1 | 3/2007 | Beselt et al. | |
| 2009/0056412 A1* | 3/2009 | Graeffe | D21G 9/0009 |
| | | | 73/1.81 |
| 2009/0059244 A1* | 3/2009 | Hellstrom | G01B 7/023 |
| | | | 356/630 |
| 2009/0087134 A1* | 4/2009 | Martinez | G01B 11/14 |
| | | | 385/12 |
| 2013/0100503 A1 | 4/2013 | Beselt | |
| 2015/0145506 A1 | 5/2015 | Aoki et al. | |

* cited by examiner

GAP AND DISPLACEMENT MAGNETIC SENSOR SYSTEM FOR SCANNER HEADS IN PAPER MACHINES OR OTHER SYSTEMS

CROSS REFERENCE TO RELATED APPLICATIONS AND CLAIM OF PRIORITY

The present application claims priority under 35 U.S.C. §119(e) to the subject matter of U.S. Provisional Patent Application Ser. No. 62/074,186 entitled "GAP AND DISPLACEMENT MAGNETIC SENSOR SYSTEM FOR SCANNER HEADS IN PAPER MACHINES OR OTHER SYSTEMS," filed on Nov. 3, 2014. The content of the above identified patent documents is incorporated herein by reference.

TECHNICAL FIELD

This disclosure relates generally to scanning systems. More specifically, this disclosure relates to a gap and displacement magnetic sensor system for scanner heads in paper machines or other systems.

BACKGROUND

Sheets or other webs of material are used in a variety of industries and in a variety of ways. These materials can include paper, multi-layer paperboard, and other products manufactured or processed in long webs. As a particular example, long sheets of paper can be manufactured and collected in reels.

It is often necessary or desirable to measure one or more properties of a web of material as the web is being manufactured or processed. Adjustments can then be made to the manufacturing or processing system to ensure that the properties stay within desired ranges. Measurements are often taken using scanners that move scanner heads containing sensors back and forth across the width of the web.

Flat web scanners typically utilize two scanner heads, one above a web and one below the web, that need to be kept in constant alignment with each other in order to minimize errors in process readings. Secondary sensors are often used as diagnostic sensors to ensure head-to-head alignment in three primary directions, namely the X (cross direction), Y (machine direction), and Z (head-to-head gap) directions. Potential interference from the web typically limits the sensor technologies that can be used for measuring the Z gap distance to magnetic, capacitive, or inductive sensing types because opaque web materials often block optical sensors. While relatively low-cost magnetic field orientation sensors exist to allow accurate displacement sensing for X and Y directions, an absolute Z gap measurement has traditionally been limited to the use of expensive inductive coil technologies.

SUMMARY

This disclosure provides a gap and displacement magnetic sensor system for scanner heads in paper machines or other systems.

In a first example, a method includes generating a magnetic field. The method includes capturing, by multiple magnetic field orientation sensors, measurements of the magnetic field. The method includes identifying, using the measurements of the magnetic field, (i) a displacement of first and second scanning sensor heads in a first direction, and (ii) a gap separation of the first and second scanning sensor heads in a second direction. At least one of the magnetic field orientation sensors is disposed offset from a centerline of the magnetic field such that an output from the at least one magnetic field orientation sensor measures a combination of the gap separation and the displacement in the first direction.

In a second example, a multiple-sensor assembly includes multiple magnetic field orientation sensors configured to capture measurements of a magnetic field in order to identify (i) a displacement of first and second scanning sensor heads in a first direction, and (ii) a gap separation of the first and second scanning sensor heads in a second direction. At least one of the magnetic field orientation sensors is disposed offset from a centerline of the magnetic field such that an output from the at least one magnetic field orientation sensor indicates a combination of the gap separation and the displacement in the first direction.

In a third example, a system includes first and second scanning sensor heads. Each of the first and second scanning sensor heads is configured to move across a surface of web of material and capture measurements associated with the web. The first scanning sensor head includes a magnet configured to generate a magnetic field. The second scanning sensor head includes multiple magnetic field orientation sensors configured to capture measurements of a magnetic field in order to identify (i) a displacement of first and second scanning sensor heads in a first direction, and (ii) a gap separation of the first and second scanning sensor heads in a second direction. At least one of the magnetic field orientation sensors is disposed offset from a centerline of the magnetic field such that an output from the at least one magnetic field orientation sensor indicates a combination of the gap separation and the displacement in the first direction.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 9, discussed below, and the various examples used to describe the principles of the present invention in this patent document are by way of illustration only and should not be construed in any way to limit the scope of the invention. Those skilled in the art will understand that the principles of the present invention may be implemented in any suitable manner and in any type of suitably arranged device or system.

Figure 1:
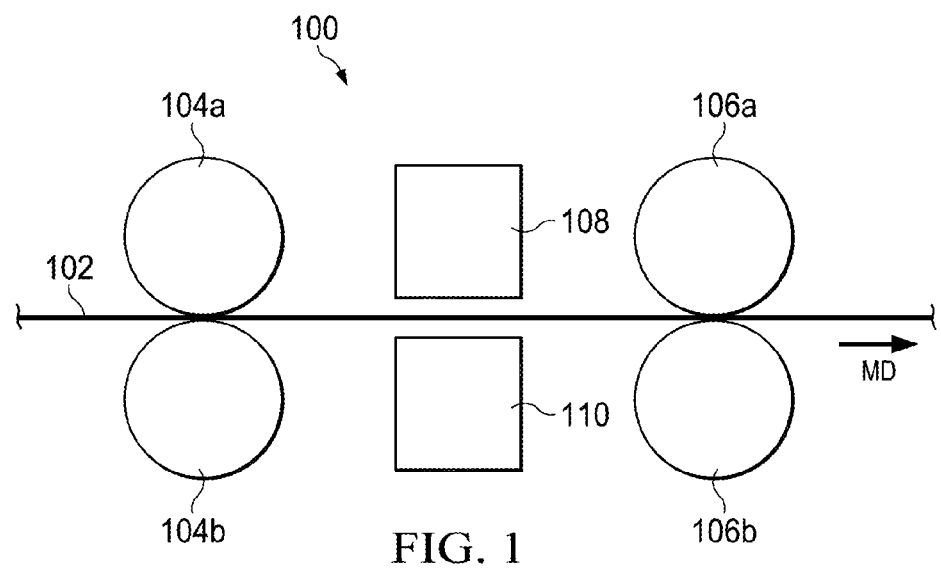
FIG. 1 illustrates a portion of an example web-making or web-processing system in accordance with this disclosure.

FIG. 1 illustrates a portion of an example web-making or web-processing system 100 in accordance with this disclosure. As shown in FIG. 1, the system 100 manufactures or processes a continuous web 102. The web 102 can represent any suitable material or materials manufactured or processed as moving sheets or other webs. Example webs 102 can include paper, multi-layer paperboard, cardboard, plastic, textiles, or metal webs.

In this example, the web 102 is transported through this portion of the system 100 using two pairs of rollers 104a-104b and 106a-106b. For example, the roller pair 104a-104b can pull the web 102 from a previous stage of a web-manufacturing or web-processing system. Also, the roller pair 106a-106b can feed the web 102 into a subsequent stage of the web-manufacturing or web-processing system. The roller pairs 104a-104b and 106a-106b move the web 102 in a direction referred to as the "machine direction" (MD).

Two or more scanning sensor assemblies 108-110 are positioned between the roller pairs 104a-104b and 106a-106b. Each scanning sensor assembly 108-110 includes one or more sensors capable of measuring at least one characteristic of the web 102. For example, the scanning sensor assemblies 108-110 could include sensors for measuring the moisture, caliper, anisotropy, basis weight, color, gloss, sheen, haze, surface features (such as roughness, topography, or orientation distributions of surface features), or any other or additional characteristic(s) of the web 102. In general, a characteristic of the web 102 can vary along the length of the web 102 (in the "machine direction") and/or across the width of the web 102 (in a "cross direction" or "CD"). Each scanning sensor assembly 108-110 includes any suitable structure or structures for measuring or detecting one or more characteristics of a web. Each scanning sensor assembly 108-110 is configured to move back and forth (in the cross direction) across the web 102 in order to measure one or more characteristics across the width of the web 102.

Each scanning sensor assembly 108-110 can communicate wirelessly or over a wired connection with an external device or system, such as a computing device that collects measurement data from the scanning sensor assemblies 108-110. For example, each scanning sensor assembly 108-110 could communicate with an external device or system to synchronize a clock of that scanning sensor assembly 108-110 with the clock of the external device or system. Each scanning sensor assembly 108-110 could also communicate with an external device or system to provide web measurements to the external device or system.

As noted above, a scanner could include multiple scanner heads, such as one above the web 102 and one below the web 102, that need to be kept in substantially constant alignment with each other in X, Y, and Z directions as the scanner heads move. The X direction could refer to the cross direction (CD) across the shorter width of the web 102, and the Y direction could refer to the machine direction (MD) along the longer length of the web 102. Differences between the positions of the scanning sensor heads in the X direction or the Y direction are referred to as displacement. The Z direction could refer to the direction in which the distance between the scanning sensor heads can be measured, which is referred to as a gap. The gap between the scanning sensor heads should be maintained at a nominal target distance that is specified. For example the nominal target distance can be specified by a user selection, or selected based on a characteristic of the web 102 to be processed by the system 100.

As described in more detail below, the scanning sensor assemblies 108-110 support a technique that allows Z gap measurements to be made of the gap between scanning sensor heads without relying on costly inductive coil-based sensors. Instead, a magnetic field orientation sensor can be used for the Z gap measurements. Other magnetic field orientation sensors could be used to capture X and Y displacement measurements. The Z gap measurements indicate how much the gap varies from the nominal target distance. Overall, this approach can be used to help maintain substantially constant alignment of scanning sensor heads while reducing the costs associated with the scanning sensor assemblies 108-110. Additional details regarding possible implementations of a scanner are provided below with respect to FIGS. 2, 3A, and 3B.

Although FIG. 1 illustrates a portion of one example web-making or web-processing system 100, various changes may be made to FIG. 1. For example, while the scanning sensor assemblies 108-110 are shown here as being used between two pairs of rollers, the scanning sensor assemblies 108-110 could be used in any other or additional location(s) of a web-making or web-processing system. Moreover, FIG. 1 illustrates one operational environment in which scanning sensor heads can be used. This functionality could be used in any other type of system.

Figure 2:
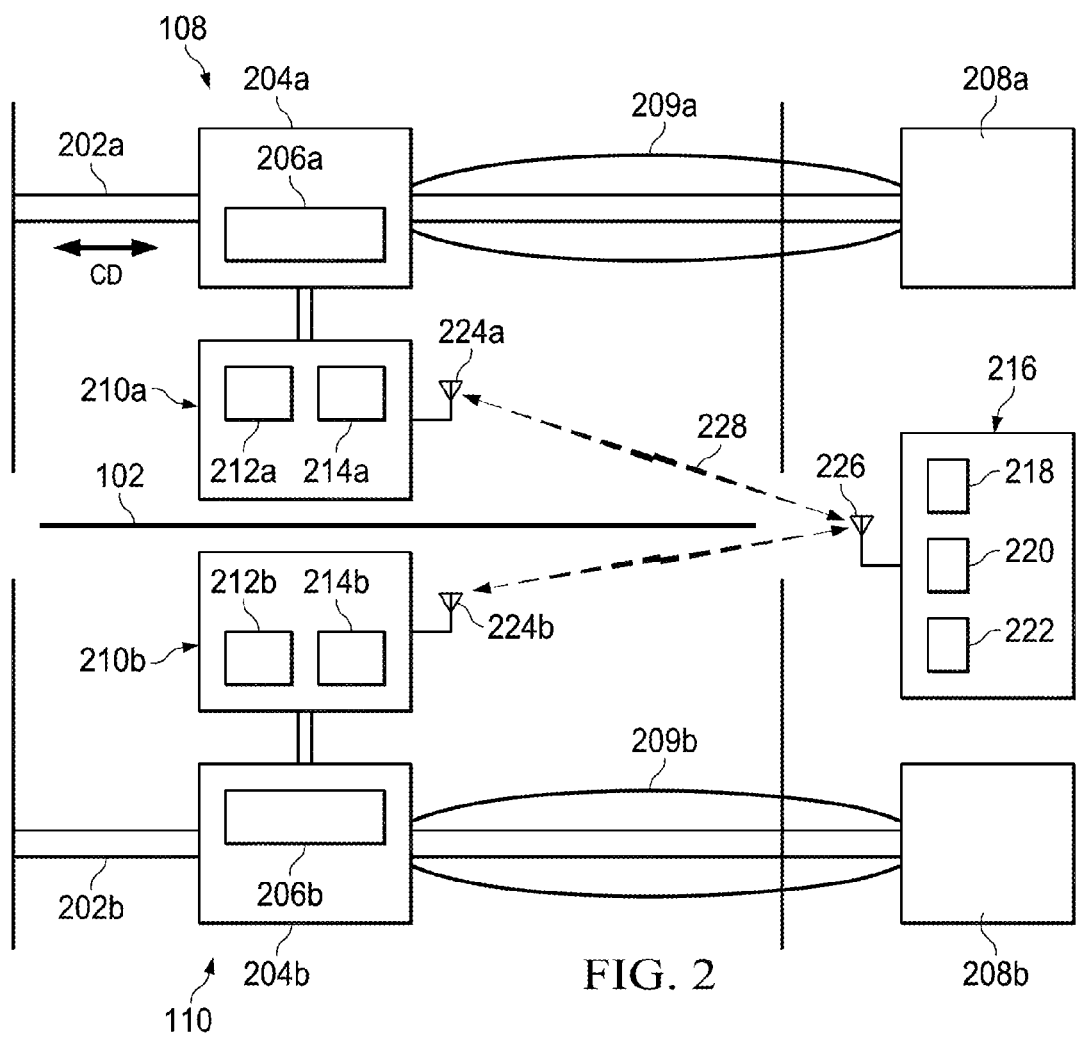
FIG. 2 illustrates an example scanner in the system of FIG. 1 in accordance with this disclosure.

FIG. 2 illustrates an example scanner in the system 100 of FIG. 1 in accordance with this disclosure. The scanner here includes the scanning sensor assemblies 108-110, which are located on opposing sides of the web 102. As shown in FIG. 2, each scanning sensor assembly 108-110 includes a respective track 202a-202b on which a respective carriage 204a-204b travels. In the system 100, each track 202a-202b could generally extend in the cross direction across the width of the web 102. Each carriage 204a-204b can traverse back and forth along its track 202a-202b to move one or more sensors back and forth across the web 102. Each track 202a-202b generally includes any suitable structure on which other components of a sensor assembly can move, such as a belt, shaft, or beam formed of metal or another suitable material. Each carriage 204a-204b includes any suitable structure for moving along a track.

Various mechanisms can be used to move the carriages 204a-204b along the tracks 202a-202b or to position the sensor assemblies 108-110 at particular locations along the tracks 202a-202b. For example, each carriage 204a-204b could include a respective motor 206a-206b that moves the carriage 204a-204b along its track 202a-202b. As another example, external motors 208a-208b could move belts 209a-209b that are physically connected to the carriages 204a-204b, where the belts 209a-209b move the carriages 204a-204b along the tracks 202a-202b. Any other suitable mechanism for moving each carriage 204a-204b along its track 202a-202b could be used.

Scanning sensor heads 210a-210b are connected to the carriages 204a-204b. Each sensor head 210a-210b respectively includes at least one web sensor 212a-212b that captures measurements associated with the web 102. Each sensor head 210a-210b includes any suitable structure for carrying one or more sensors. Each web sensor 212a-212b includes any suitable structure for capturing measurements associated with one or more characteristics of a web. A web sensor 212a-212b could represent a contact sensor that takes measurements of a web via contact with the web or a non-contact sensor that takes measurements of a web without contacting the web.

Each sensor head 210a-210b also respectively includes at least one position sensor element 214a-214b for capturing gap and displacement measurements associated with the sensor heads 210a-210b. As described in more detail below, the position sensor element 214a in the sensor head 210a could represent a magnet or other magnetic field generator. Also, the position sensor element 214b in the sensor head 210b could include multiple magnetic field orientation sensors. Of course, the sensor head 210a could include the magnetic field orientation sensors, and the sensor head 210b could include the magnetic field generator.

Power can be provided to each sensor head 210a-210b in any suitable manner. For example, each sensor head 210a-210b could be coupled to one or more cables that provide power to that sensor head. As another example, each carriage 204a-204b could ride on one or more cables or rails used to supply power to the associated sensor head 210a-210b. Each sensor head 210a-210b could further include an internal power supply, such as a battery or an inductive coil used to receive power wirelessly. Each sensor head 210a-210b could be powered in any other or additional manner.

In this example, each sensor head 210a-210b can send sensor measurement data to an external controller 216. The controller 216 could use the measurement data in any suitable manner. For example, the controller 216 could use the measurement data to generate CD profiles of the web 102. The controller 216 could then use the CD profiles to determine how to adjust operation of the system 100. The controller 216 could also use the CD profiles or the measurement data to support monitoring applications, process historian applications, or other process control-related applications.

The controller 216 includes any suitable structure(s) for receiving sensor measurement data, such as one or more computing devices. In particular embodiments, the controller 216 includes one or more processing devices 218, such as one or more microprocessors, microcontrollers, digital signal processors, field programmable gate arrays, or application specific integrated circuits. The controller 216 also includes one or more memories 220, such as one or more volatile and/or non-volatile storage devices, configured to store instructions and data used, generated, or collected by the processing device(s) 218. In addition, the controller 216 includes one or more interfaces 222 for communicating with external devices or systems, such as one or more wired interfaces (like an Ethernet interface) or one or more wireless interfaces (like a radio frequency transceiver). The controller 216 could represent all or part of a centralized control system or part of a distributed control system. In particular embodiments, the controller 216 includes a measurement subsystem (MSS), which interacts with the sensor assemblies 108a-108b to obtain and process measurements of the web 102. The processed measurements can then be provided to other components of the controller 216.

Each sensor head 210a-210b and the controller 216 can communicate wirelessly or via a wired connection. In the embodiment shown in FIG. 2, each sensor head 210a-210b is configured for wireless communication and respectively includes at least one antenna 224a-224b, and the controller 216 includes at least one antenna 226. The antennas 224-226 support the exchange of wireless signals 228 between the sensor heads 210a-210b and the controller 216. For example, the controller 216 could transmit commands instructing the sensor heads 210a-210b to capture measurements of the web 102, and the sensor heads 210a-210b can transmit web measurements to the controller 216. Additionally, the controller 216 could transmit commands instructing the sensor heads 210a-210b to capture gap and displacement measurements associated with the sensor heads 210a-210b, and the sensor heads 210a-210b can transmit gap and displacement measurements to the controller 216. The sensor heads 210a-210b could also transmit other data to the controller 216, such as diagnostic data. Each antenna 224a, 224b, 226 includes any suitable structure for transmitting wireless signals, such as radio frequency signals.

Although FIG. 2 illustrates one example of a scanner in the system 100 of FIG. 1, various changes may be made to FIG. 2. For example, various components in each scanning sensor assembly 108-110 could be combined, further subdivided, or omitted and additional components could be added according to particular needs. Also, the form of each assembly with a carriage 204a-204b connected to a separate sensor head 210a-210b is for illustration only. Each sensor head 210a-210b could incorporate or be used with a carriage in any suitable manner.

Figure 3A:
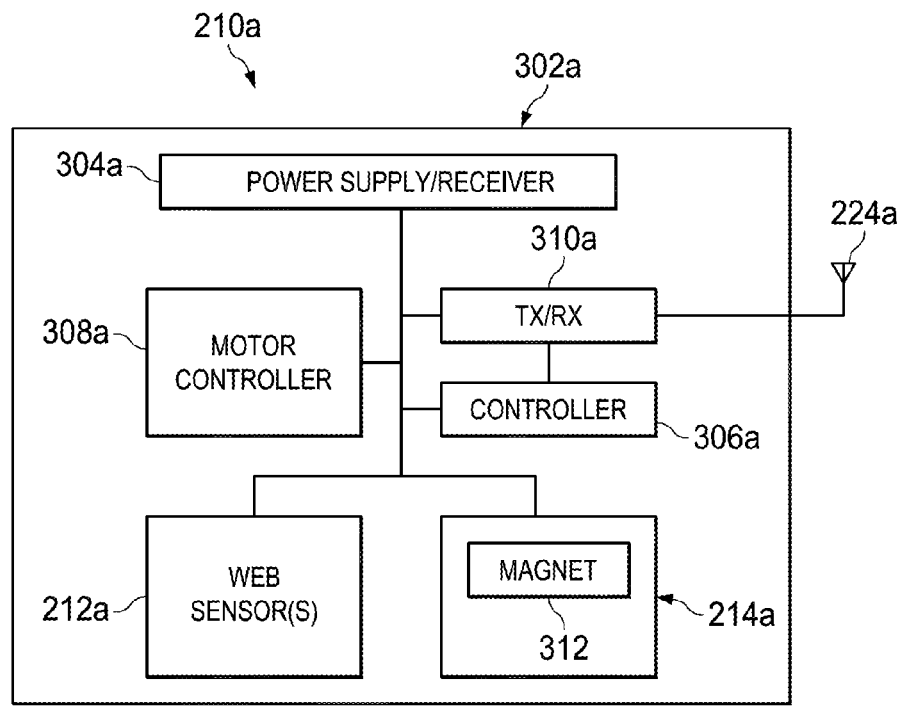
FIGS. 3A and 3B illustrate example scanning sensor heads in the scanner of FIG. 2 in accordance with this disclosure.
Figure 3B:
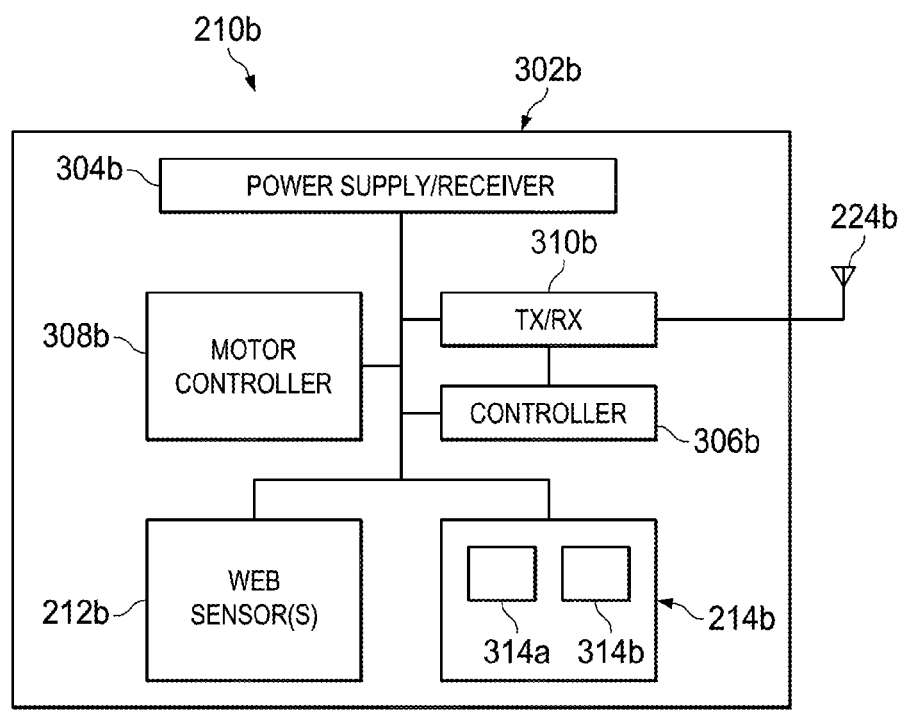

FIGS. 3A and 3B illustrate example scanning sensor heads 210a-210b in the scanner of FIG. 2 in accordance with this disclosure. As shown in FIG. 3A, the scanning sensor head 210a includes one or more web sensors 212a and the position sensor element 214a. The scanning sensor head 210a also includes a moveable chassis 302a, which represents a housing or other structure configured to encase, contain, or otherwise support other components of the scanning sensor head 210a. The chassis 302a can be formed from any suitable material(s) (such as metal) and in any suitable manner.

A power supply/receiver 304a provides operating power to the scanning sensor head 210a. For example, the power supply/receiver 304a could receive AC or DC power from an external source, and the power supply/receiver 304a could convert the incoming power into a form suitable for use in the scanning sensor head 210a. The power supply/receiver 304a includes any suitable structure(s) for providing operating power to the scanning sensor head 210a, such as an AC/DC or DC/DC power converter. The power supply/receiver 304a may also or alternatively include a battery, capacitor, or other power storage device.

A controller 306a controls the overall operation of the scanning sensor head 210a. For example, the controller 306a could receive and optionally process measurements associated with one or more characteristics of the web 102 from the web sensor 212a. The controller 306a could also control the transmission of this data to the controller 216 or other destination(s). The controller 306a includes any suitable processing or control device(s), such as one or more microprocessors, microcontrollers, digital signal processors, field programmable gate arrays, or application specific integrated circuits. Note that the controller 306a could also be implemented as multiple devices.

A motor controller 308a can be used to control the operation of one or more motors, such as one or more of the motors 206a-206b, 208a-208b. For example, the motor controller 308a could generate and output pulse width modulation (PWM) or other control signals for adjusting the direction and speed of the motor 206a. The direction and speed could be controlled based on a command or other input from the controller 306a. The motor controller 308a includes any suitable structure for controlling operation of a motor.

A wireless transceiver 310a is coupled to the antenna(s) 224a. The wireless transceiver 310a facilitates the wireless transmission and reception of data, such as by transmitting web measurements, positional measurements, and related data to the controller 216 and receiving commands from the controller 216. The wireless transceiver 310a includes any suitable structure for generating signals for wireless transmission and/or for processing signals received wirelessly. In particular embodiments, the wireless transceiver 310a represents a radio frequency (RF) transceiver. Note that the transceiver 310a could be implemented using a transmitter and a separate receiver.

As shown in FIG. 3B, the scanning sensor head 210b could include many or all of the same components as the scanning sensor head 210a. As shown here, the scanning sensor head 210b includes one or more web sensors 212b and the position sensor element 214b. The scanning sensor head 210b also includes a housing 302b, a power supply/receiver 304b, a controller 306b, a motor controller 308b, and a transceiver 310b. These components are the same as or similar to the corresponding components in the scanning sensor head 210a, so a detailed description of each of these will not be repeated.

In some embodiments, the position sensor element 214a in the scanning sensor head 210a includes a magnet 312, and the position sensor element 214b in the scanning sensor head 210b includes magnetic field orientation sensors 314a-314b. As described above, the magnetic field orientation sensors 314a-314b are low cost sensors that provide accurate displacement sensing. In this approach, magnetic field orientation sensor(s) 314a can be used to sense the magnetic field generated by the magnet 312 to identify displacement measurements in either the X or Y direction. Moreover, an additional magnetic field orientation sensor 314b is used in an offset orientation from the centerline of a magnetic field to measure the Z gap distance between the sensor heads 210a-210b. In this location, the angle of the magnetic field lines changes as the distance between the magnet 312 and the magnetic field orientation sensor 314b changes. This change in angle can be calibrated to be linear over a working range and is practical for use in certain gaps (such as those up to about 25 mm plus a tolerance) with decreasing sensitivity as the distance across the gap increases, as long as the magnetic field strength is high enough for proper sensor saturation. As an example, the tolerance could be ±2 or ±3 millimeters (mm) for a nominal target gap of 10 mm, or the tolerance could be up to approximately ±5 mm for a nominal target gap of 25 mm.

For each of the magnetic field orientation sensors 314a-314b, because the field angle also changes with lateral motion (in the CD or MD) between the magnet 312 and the magnetic field orientation sensor, a correction factor can be generated by an additional magnetic field orientation sensor situated in the same plane, such as one magnetic field orientation sensor centered on the 0° degree flux line of the magnetic field. The centerline of the magnetic field is located along the 0° degree flux line, which could be located along a centerline of the magnet 312. This additional sensor (which may represent one of the magnetic field orientation sensors 314a already present to take either X or Y displacement readings) need not add cost to the system and is relatively insensitive to Z gap variations over the desired operating range (such as about ±3 mm of gap on a 10 mm nominal target gap). In this arrangement, the output of the magnetic field orientation sensor 314b is a combination of both Z and X (or Z and Y) direction displacement in that plane, but the X (or Y) sensor 314a is sensitive only to X (or Y) sensor displacement. Therefore, a component of the output from the Z sensor 314b can be calculated from the output of the X (or Y) sensor 314a and subtracted from the reading from the Z sensor 314b to allow the combination of sensors 314a-314b to give independent readings of X (or Y) and Z displacement. The Y (or X) sensor 314a can be mounted on a circuit board aligned with the magnet centerline in an orthogonal plane to capture readings in the third dimension. As described in more particular detail below with reference to FIGS. 4-10, a magnetic field orientation sensor 314a (sensitive only to X displacement) is centered on the 0° degree flux line of the magnetic field and located in the same plane as the second magnetic field orientation sensor 314b; and another magnetic field orientation sensor 314a (sensitive only to Y displacement) is located in a plane that is also centered on the 0° degree flux line of the magnetic field and orthogonal to the plane of the second magnetic field orientation sensor 314b.

In particular embodiments, three magnetic field orientation sensors 314a-314b (such as HONEYWELL HMC1501/1502 sensors) are mounted in two right-angle planes that intersect the centerline of the magnetic field of an elongated permanent magnet 312. Two of the magnetic field orientation sensors (either the X and Z sensors or the Y and Z sensors) are located in one plane such that the Z sensor is laterally offset from the center of the magnet 312 and the X or Y sensor is situated on the magnet centerline. A third Y or X sensor is mounted in a plane at right angles to the other sensors and bisecting the magnet. The use of an elongated magnet 312 in the X or Y direction can help to reduce variations in field angle for the other directions when large X or Y displacements are encountered, while also maintaining sensitivity in the other directions and keeping magnet sizes practical.

Although FIGS. 3A and 3B illustrate examples of scanning sensor heads 210a-210b in the scanner of FIG. 2, various changes may be made to FIGS. 3A and 3B. For example, various components in FIGS. 3A and 3B could be combined, further subdivided, or omitted and additional components could be added according to particular needs. As a particular example, a single controller or more than two controllers could be used to implement the functions of the controllers 306a-306b and 308a-308b. Additionally or alternatively, one or both controllers 306a/308a or 306b/308b could be located external to the scanning sensor head 210a/210b, such as at the external controller 216 or at any other suitable location. In certain embodiments, the motor controller 308a is a master to the slave motor controller 308b, such that the slave motor controller 308b adjusts the speed and direction of the motor 206b based on the displacement or variance from head-to-head alignment in the X-direction. That is, the slave motor controller 308b is configured to modulate and output a control signal to maintain head-to-head alignment in the X-direction.

Figure 4:
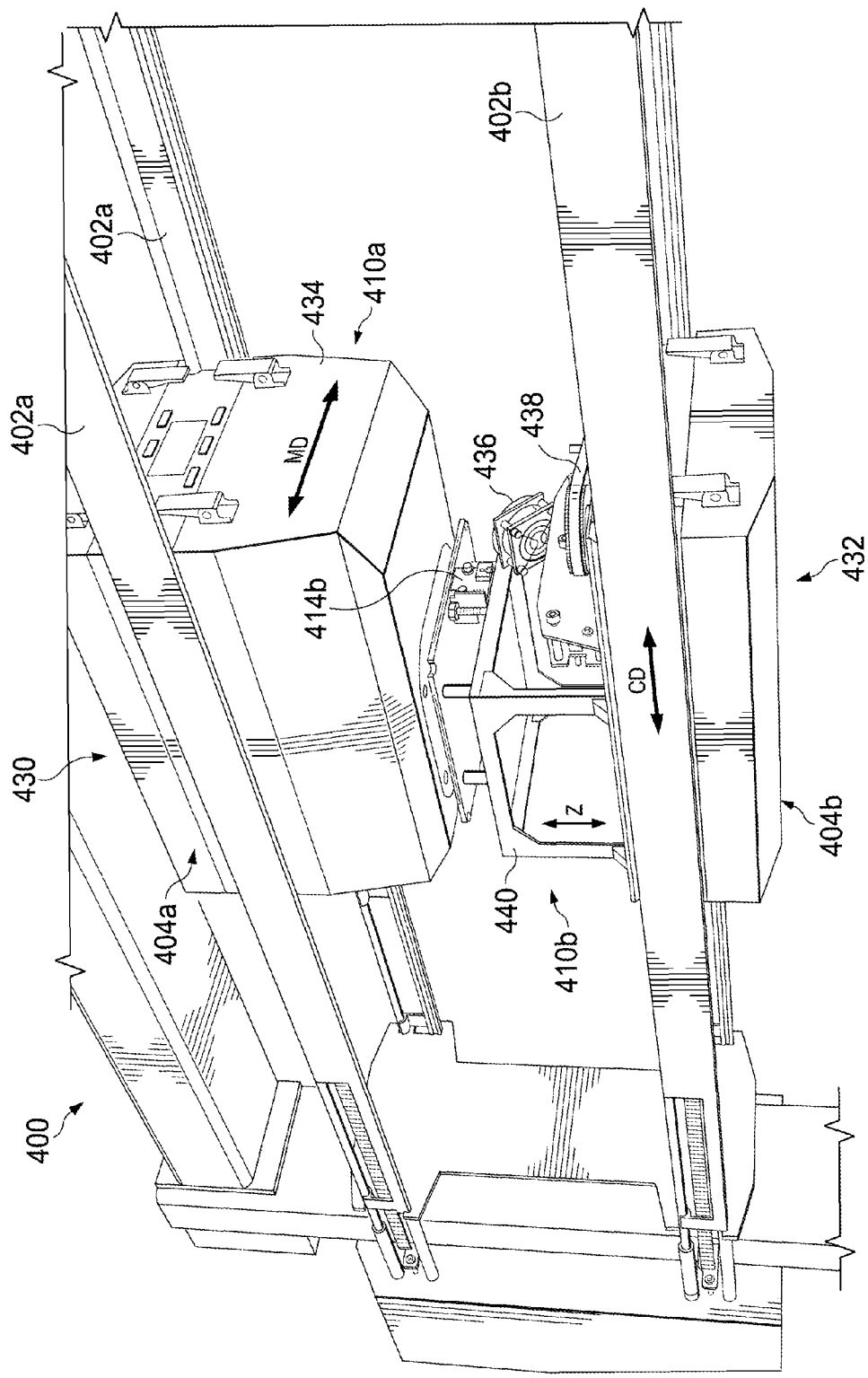
FIG. 4 illustrates a perspective view of a portion of an example web-making or web-processing system in accordance with this disclosure.

FIG. 4 illustrates a perspective view of a portion of an example web-making or web-processing system in accordance with this disclosure. The embodiment of the system 400 shown in FIG. 4 is for illustration only. Other embodiments could be used without departing from the scope of the present disclosure.

The system 400 could, for example, be the system 100 of FIG. 1. Note that the scanner including scanning sensor assemblies 430-432 in FIG. 4 could be the same as or similar to the scanner including scanning sensor assemblies 108-110 in FIGS. 1 and 2. Also note that the scanning sensor heads 410a-410b in FIG. 4 could be the same as or similar to the scanning sensor heads 210a-210b in FIGS. 2, 3A, and 3B.

These components in FIG. 4 can operate in the same or similar manner as the corresponding components in FIGS. 1, 2, 3A, and 3B.

The scanning sensor head 410a is shown with a cover 434 such that the components housed within the cover 434 are hidden from view. The cover 434 forms part of the moveable chassis (such as the moveable chassis 302a-302b) of the sensor head 410a. Each sensor head 410a-410b respectively includes at least one web sensor that captures measurements associated with a web, such as the web 102.

The scanning sensor head 410b is shown without a cover such that the components housed within the cover are visible. The scanning sensor head 410b includes the position sensor element 414b, a fan 436, a pulley and belt system 438, and a frame 440 to which the position sensor element 414b is mounted.

Scanning sensor heads 410a-410b are connected to the carriages 404a-404b. Each carriage 404a-404b traverses back and forth along its track 402a-402b to move one or more sensors back and forth across a web, such as the web 102. That is, the sensor heads 410a-410b move together, such as in unison, with the carriages 404a-404b. Accordingly, movement of the carriage 404a-404b correspondingly moves the web sensors (such as web sensors 212a-212b) and the position sensor element 414b that are within the sensor head 410a-410b.

For orientation, an arrow labeled CD indicates a "cross direction" or X-Direction across the width of the web 102. Another arrow labeled MD indicates the "machine direction" or Y-Direction along the length of the web 102. Another arrow labeled Z indicates the direction in which the Z gap separation distance between the scanning sensor heads is measured.

Figure 5:
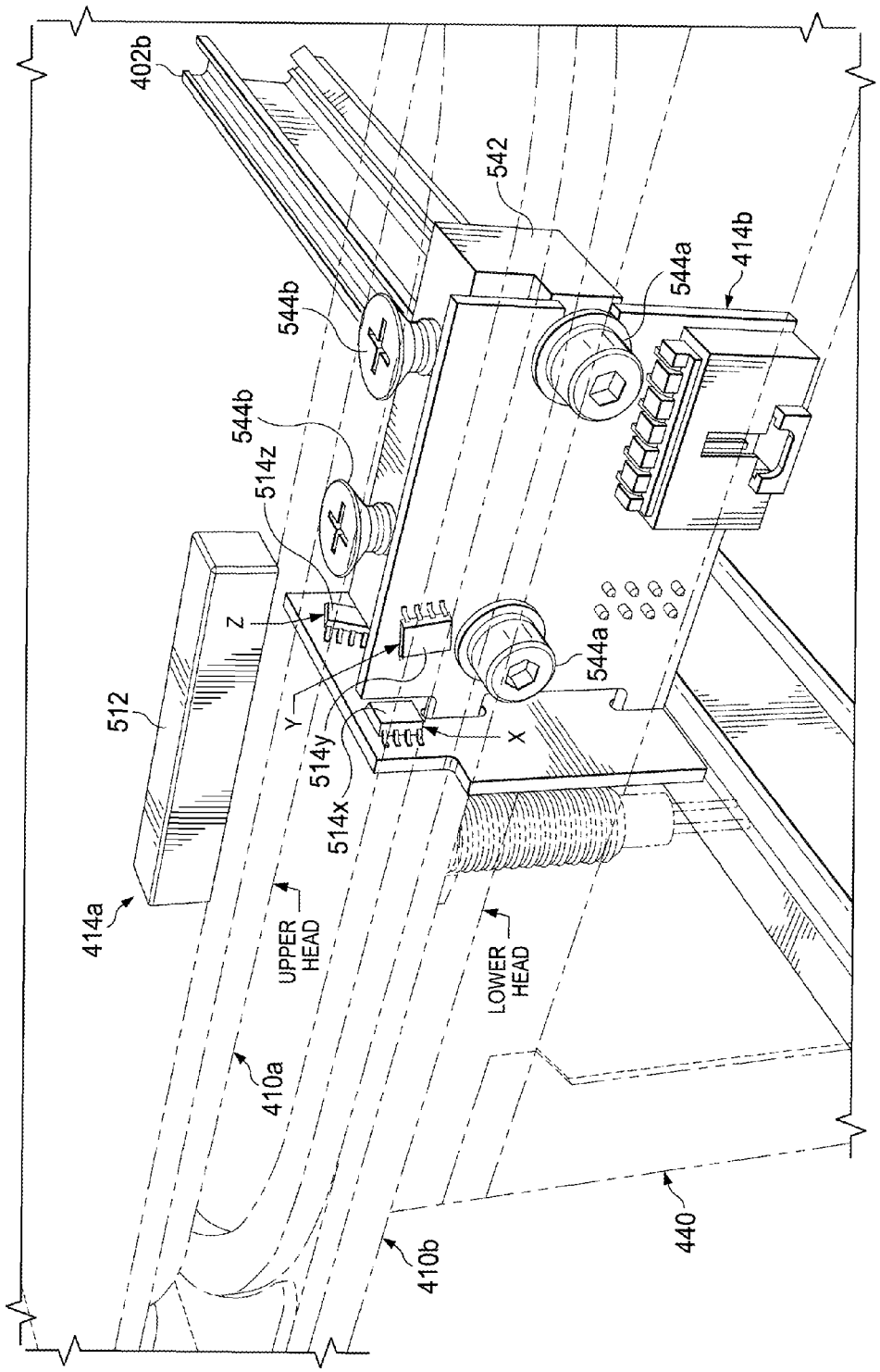
FIGS. 5 and 6 illustrate orthogonal views of the position sensor elements within the scanner of FIG. 4.
Figure 6:
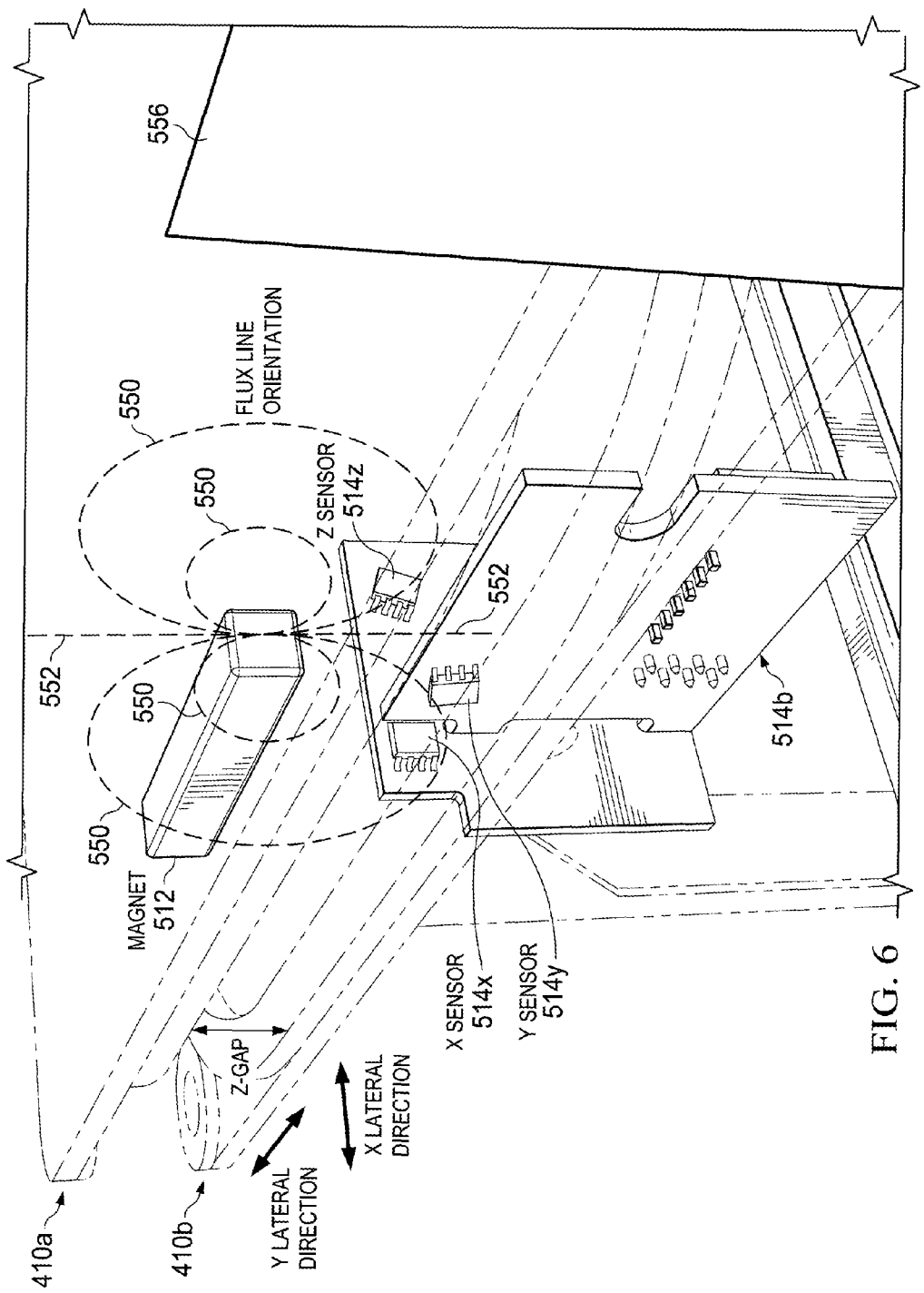

FIGS. 5 and 6 illustrate orthogonal views of the position sensor elements 414a-414b within the scanner of FIG. 4. Other components of the upper sensor head 410a and lower sensor head 410b are faintly shaded or translucent to show placement relative to the position sensor elements 414a-414b, which are shown as opaquely shaded or solid. For example, the track 402b and frame 440 are faintly visible.

As shown in FIG. 5, the position sensor element 414a includes a magnetic field generator, such as the magnet 512. The magnet 512 could be the same as or similar to the magnet 312 described in FIG. 3A. The magnet 512 can be composed from a rare earth magnetic material. The position sensor element 414a can include a casing (such as a chrome plating or cladding) for the magnet 512 to shield the magnet from being exposed to corrosion causing environmental factors.

The position sensor element 414b includes three magnetic field orientation sensors: an X-sensor 514x, a Y-sensor 514y, and a Z-sensor 514z. The X-sensor 514x could be the same as the magnetic field orientation sensor 314a and sensitive only to X-displacement. Similarly, the Y-sensor 514y and Z-sensor 514z could be the same as the magnetic field orientation sensors 314a and 314b, respectively, and sensitive only to Y-displacement or Z gap separation, respectively. The position sensor element 414b also includes a head XYZ sensor alignment block 542 that includes various screws or other alignment elements 544a, 544b. The operation of the magnetic field orientation sensors 514x-514z is described more particularly below in reference to FIGS. 7 and 8.

As shown in FIG. 6, the magnet 512 has an elongated rectangular prism shape, such as a geometrical elongated square prism. One pole (namely, the north-seeking pole or the south-seeking pole) of the magnet 512 is located at the top of the magnet 512, and the other pole is located at the bottom of the magnet. Accordingly, the magnet 512 produces an elongated magnetic field. The front face of the magnet 512 produces a magnetic field represented by the magnetic field lines 550, 552 that originate from the centerpoint and spread out in the XZ plane. A longitudinal cross-section of the magnet 512 would produce similar magnetic field lines 550, 552 in the XZ plane. The magnetic field lines 552 are disposed at a centerline of the magnet 512. The magnetic field lines 552 are straight and vertical, representing a zero degree (0°) magnetic field orientation of the magnetic flux along the centerline of the magnet. By comparison, the magnetic field lines 550 are curved, such as into ellipses or circles that are tangent to the magnetic field line 552. The curvature of the magnetic field lines 550 changes according to the distance from the zero degree (0°) line 552.

In certain embodiments, the elongated size of the magnet reduces to a negligible level over the expected operation range in the Y-Direction change in shape of the magnetic field that the X and Z sensors sense. In other words, the magnetic field lines at a longitudinal cross-section at the centerline of the magnet has the shape of the magnetic field lines 550, 552. Any longitudinal cross-section within a defined displacement range (for example, ±5 mm, depending on the size of the magnet) in the Y-Direction from the centerline of the magnet, the field lines field lines in the XZ plane that intersect the X-sensor 514x and Z-sensor 514z have substantially the same shape of the magnetic field lines 550, 552. The expected operation range of the sensors 514x and 514z is within the defined displacement range. Within the expected operation range, errors can be neglected or corrected for by the other sensor' readings. When comparing the longitudinal cross-section at the centerline to a second longitudinal cross-section at different Y-point within the defined displacement range, any difference the in shape of the magnetic field lines is negligible from the perspective of the X-sensor 514x and Z-sensor 514z. However, a third longitudinal cross-section from a Y-point far enough away from the centerline towards the ends of the magnet, beyond the defined displacement range, would show that the field lines tighten inwards. That is, from the perspective of the X-sensor 514x and Z-sensor 514z, the third longitudinal cross-section has a non-negligible difference in shape from the centerline longitudinal cross-section, that would cause an error in the Z calibration. In a similarly manner, the Y-sensor 514y has defined displacement range in the X-Direction from the centerline of the magnet.

The YZ plane 556 is aligned with the 0° line 552 (e.g., centerline of the magnet) and orthogonal to the front face of the magnet 512. That is, the YZ plane 556 bisects the magnet 512, and the magnet 512 produces straight and vertical magnetic field lines that have a 0° magnetic field orientation in the YZ plane. The upper sensor head 410a and lower sensor head 410b are separated by a nominal target distance shown as the "Z-gap."

Figure 7:
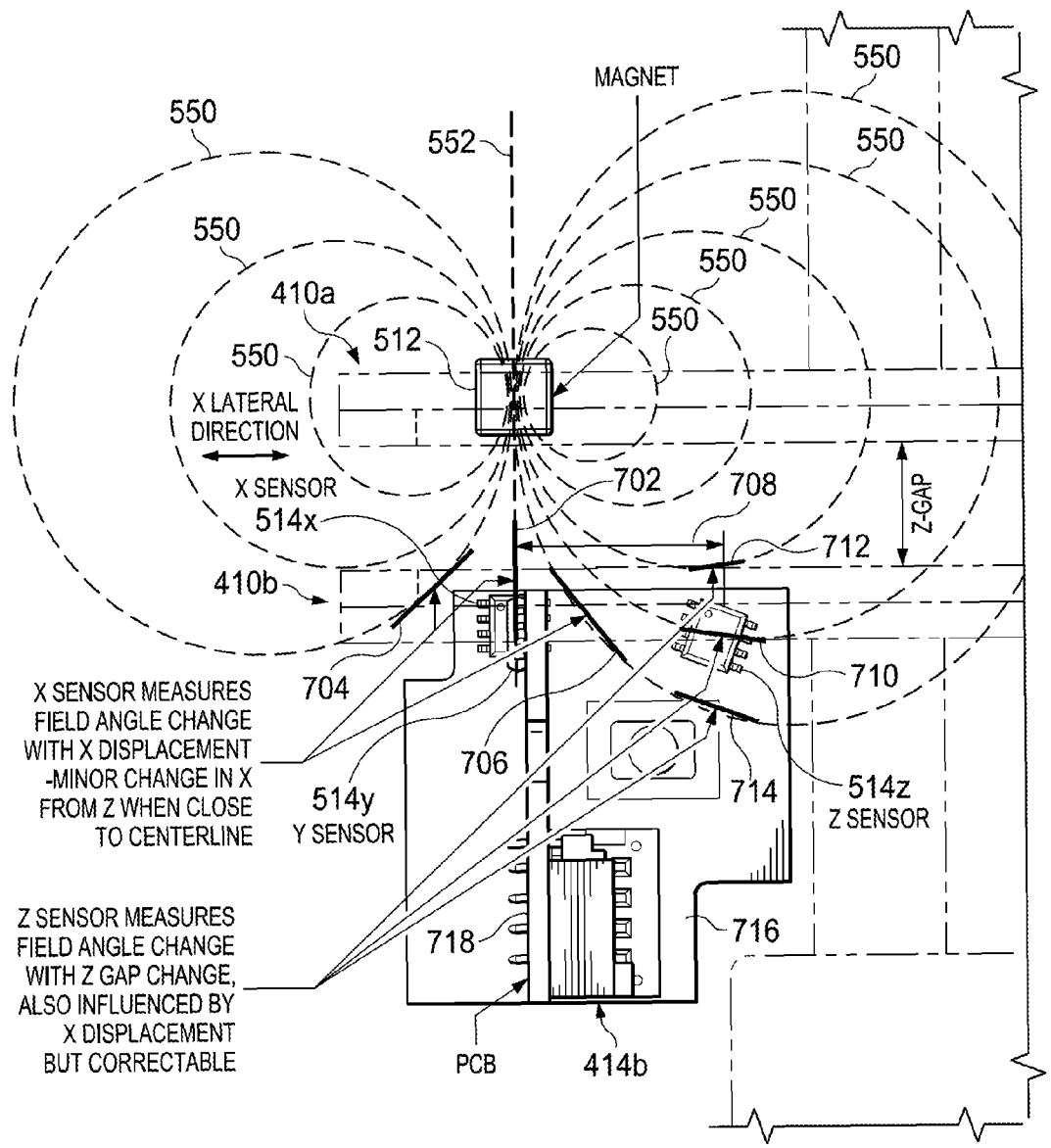
FIG. 7 illustrates the position sensor elements within the scanner of FIG. 4 according to a projection of the X-Z plane.

FIG. 7 illustrates the position sensor elements within the scanner of FIG. 4 according to a projection of the X-Z plane. The position sensor elements 414a-414b are shown as opaquely shaded, while other components of the upper sensor head 410a and lower sensor head 410b are faintly shaded or translucent to show placement relative to the position sensor elements 414a-414b.

The position sensor element 414b includes a multiple-sensor assembly that includes the magnetic field orientation (MFO) sensors 514x, 514y, and 514z. Each MFO sensor 514x, 514y, 514z senses and measures the orientation of the magnetic field in a plane, such as the plane in which the sensor is disposed. For example, wheatstone bridge elements in the X-sensor 514x and Z-sensor 514z only sense in an XZ plane, and in the Y-sensor, only sense in the YZ plane. In certain embodiments, an MFO sensor can sense and measure field angles in all 360° of its sensitivity plane. In other embodiments, an MFO sensor has a limited angle range and can sense and measure field angles within the limited angle range of its sensitivity plane. Each MFO sensor 514x, 514y, 514z is calibrated to operate within a linear range (also referred to as "calibration range") of its calibration curve. While a MFO sensor is calibrated to operate in the linear range of its calibration curve, in response to sensing a magnetic field that has a magnitude sufficient for proper sensor saturation, the sensor outputs a signal, wherein the voltage level of the signal is linearly related to the field angle measurement of the sensed magnetic field. That is, within the linear calibration range, the field angle measurement of the magnetic field accurately represents a linear distance from a reference point. Movement of the MFO sensor in one or more directions of sensitivity causes the MFO sensor to output a signal having a voltage level that corresponds to both (1) a linear distance away from alignment of the reference point in the direction(s) of sensitivity, and (2) a field angle different from the field angle at the reference point. Embodiments of the present disclosure are not limited to MFO sensors with linear calibration. Other embodiments can include a calibration range wherein the voltage level of the sensor output signal is related to the field angle measurement according to a curve having a higher degree of a nominal (for example, a quadratic curve).

The X-sensor 514x is aligned with the 0° magnetic field line 552 at the centerline of the magnet 512. That is, the X-sensor 514x is configured to have the 0° magnetic field line 552 as its alignment reference point, and as such, the X-sensor 514x measures field angles with reference from the 0° magnetic field line 552. While the X-sensor 514x is in head-to-head alignment with the 0° magnetic field line 552, the X-sensor 514x detects a magnetic field angle of 0° (i.e., the reference field angle) and outputs a signal having a voltage that corresponds to the 0° field angle in the linear range of the calibration curve of the X-sensor 514x. Head-to-head alignment of the X-sensor 514x corresponds to both (1) the 0° reference field angle measured at the alignment reference point, and (2) the output voltage corresponding to the 0° field angle.

While the X-sensor 514x is in head-to-head alignment with the 0° magnetic field line 552, any movement of the X-sensor 514x in the Z-Direction would cause the X-sensor 514x to generate an output voltage corresponding to the 0° of the line 702 that is parallel with the magnetic field line 552. That is, as the orientation of the magnetic field emanating from the centerline of the magnet 512 is 0° and does not vary in the Z-Direction (as shown by the straight magnetic field line 552). By aligning the X-sensor 514x at a location (i.e., at the centerline of the magnet) where the movement in the Z-Direction yields a constant 0° field angle, the X-sensor 514x becomes insensitive to Z displacement.

Further, as described above, within the defined displacement range within which differences in the shape of the magnetic field are negligible, any longitudinal cross-section of the magnet 512 in the XZ plane would yield magnetic field lines 550, 552 that have substantially the same field angle produced at the front face of the magnet. Accordingly, any movement of the X-sensor 514x in the Y-Direction (i.e., the direction in which the magnet is elongated) would yield substantially the same output from the X-sensor 514x as prior to the movement in the Y-Direction. By aligning the X-sensor 514x at a location (i.e., at the centerline of the magnet 512) where the movement in the Y-Direction yields a constant 0° field angle, the X-sensor 514x becomes insensitive to Y displacement.

By aligning the X-sensor 514x at the centerline of the magnet 512, the X-sensor 514x is sensitive only to movement in the lateral X-Direction. Any movement of the X-sensor 514x in the X-Direction causes the X-sensor 514x to measure a field angle different from the 0° alignment. Any field angle measured by the X-sensor 514x that is different from the 0° alignment corresponds to movement of the scanning sensor heads 410a-410b a linear distance away from head-to-head alignment in the X-Direction. For example, leftward movement of the X-sensor 514x in the X-Direction causes the X-sensor to detect a magnetic field orientation having a tangent line 704, while rightward movement of the X-sensor 514x in the X-Direction causes the X-sensor detect a magnetic field orientation having a tangent line 706.

The Z-sensor 514z is offset from the magnetic field line 552, that is, disposed at distance 708 away from the centerline of the magnet 512. Also, the Z-sensor 514z is canted from the magnetic field line 552 at a nonorthogonal angle in order to mid-range the sensor by aligning the sensor with the field angle that corresponds to a combination of the gap separation in the Z-Direction and in the displacement in the X-Direction. That is, the Z-sensor 514z is configured to have a reference point corresponding to head-to-head alignment in both the Z-Direction and in the X-Direction.

For example, when the lower scanning sensor head 410b is in head-to-head alignment with the upper sensor head 410a, the magnet 512 has a field orientation that is tangent to the line 710. Accordingly, the Z-sensor 514z is configured to have a reference point corresponding to the field angle of the tangent line 710. Any movement of the Z-sensor 514z in the X-Direction, the Z-Direction, or both X and Z directions causes the Z-sensor 514z to measure a field angle that is different from the angle of the tangent line 710 (i.e., the reference field angle). More particularly, movement of the Z-sensor 514z upward in the Z-direction may cause the Z-sensor to measure the field angle of the tangent line 712, wherein the change of field angle from the line 710 to the line 712 indicates an amount of reduction in the gap separation. Movement of the Z-sensor 514z downward may cause the Z-sensor to measure the field angle of the magnetic field line 550 that has a tangent line 714. The change of field angle from the line 710 to line 714 indicates an increase in the gap separation. Also, any movement of the Z-sensor 514z toward the centerline of the magnet 512 (e.g., leftward in the X-direction) causes the Z-sensor 514z to measure a reduced field angle because the magnetic field lines 550 converge toward the magnetic field line 552. Note that the magnetic field line that is tangent to line 706 has a smaller field angle (measured with reference to the magnetic field line 552) than any of the lines 710, 712, or 714 that are disposed farther away from the magnetic field line 552 in the X-Direction.

The Z-sensor 514z is substantially not sensitive to movement in the Y-direction for the same reasons that the X-sensor 514x outputs the same measurement if moved in Y-Direction, as described above with reference to the defined displacement range within which differences in the shape of the magnetic field are negligible.

For example, upward movement of the Z-sensor 514z in the Z-Direction causes the Z-sensor detect a magnetic field orientation having tangent line 712, while downward movement of the Z-sensor 514z in the Z-Direction causes the Z-sensor detect a magnetic field orientation having tangent line 714.

The Z-sensor 514z is disposed in the same plane (i.e., the XZ plane) as the X-sensor 514x, such as mounted to a same face 716 of a printed circuit board (PCB). Accordingly, displacement of the position sensor element 414b (including the PCB) correspondingly displaces the X and Z sensors 514x and 514z in unison, causes both sensors to detect the same X-direction displacement. Based on the substantially insensitivity to Z-Direction motion, the X-sensor 514x can generate a correction factor for measurements output from the Z-sensor 514z. For example, processing circuitry, such as in a controller 216, 306a-306b, can subtract a calibrated amount of the X-direction displacement measured by the X-sensor 514x from the Z-direction displacement measured by the Z-sensor 514z, to correct for displacement that have both an X and a Z component. Over a small displacement range (for example, 0-2° change in field angle) from the head-to-head alignment, a change in field angle can be converted into a distance with a simple slope and offset factor in order to adjust web sensor 22a-212b measurements. As the small displacement range increases, conversion error increases and higher order calibration equations are needed to make the conversion.

The position sensor element 414b is configured such that the field angles in the linear calibration range of the Z-sensor 514z correspond to linear distances within the tolerance corresponding to a specified nominal target gap separation. For example, if the linear calibration range is the set of angles between ±2°, and if the target gap separation is specified to a nominal value of 10 mm with a ±3 mm tolerance, then the range of linear distances corresponding to ±2° is at least ±3 mm. At one limit point of the calibration range, the head-to-head gap separation is minimum at 7 mm, where a −2° field angle accurately represents the −3 mm linear distance tolerance. At the other limit point of the calibration range, the head-to-head gap separation is maximum at 13 mm, where a +2° field angle accurately represents the +3 mm linear distance tolerance. In certain embodiments, the range of linear distances corresponding to the range of angles in the linear calibration range is greater than the tolerance. Also, the position sensor element 414b is configured such that the field angles in the linear calibration range of the X-sensor 514x and the Y-sensor 514y correspond to linear distances within a tolerance of lateral displacement in the respective X and Y directions. Note that the sensor may have a linear calibration curve for field angles beyond the calibration range, such as ±45°, but the accuracy of the equations used to convert the field angle into a linear distance decreases at field angles greater than the small range (for example, ±2°), yielding the need for higher order calibration equations to convert the field angle into a linear distance.

The Y-sensor 514y can be mounted to the same PCB, yet is disposed on a different face 718 that is orthogonal to the face 716 of the X and Z sensors 514x, 514z. The operation of the Y-sensor 514y is described in more particular detail below with reference to FIG. 8.

Figure 8:
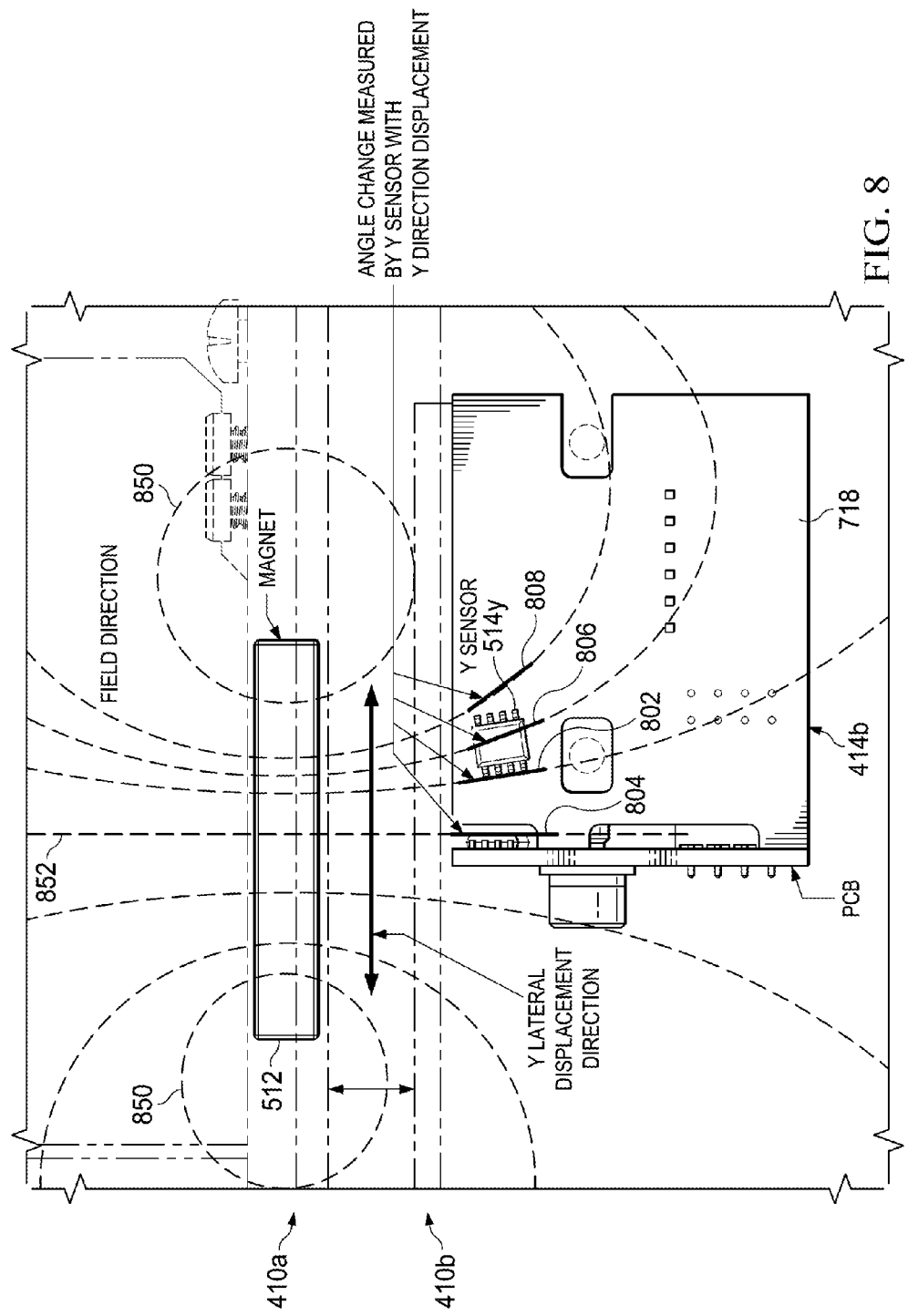
FIG. 8 illustrates the position sensor elements within the scanner of FIG. 4 according to a projection of the Y-Z plane.

FIG. 8 illustrates the position sensor elements within the scanner of FIG. 4 according to a projection of the Y-Z plane. The position sensor elements 414a-414b are shown as opaquely shaded, while other components of the upper sensor head 410a and lower sensor head 410b are faintly shaded or translucent to show placement relative to the position sensor elements 414a-414b.

The side face of the magnet 512 produces a magnetic field represented by the magnetic field lines 850, 852 that originate from the centerpoint and spread out in the YZ plane. A lateral cross-section of the magnet 512 would produce similar magnetic field lines 850, 852 in the YZ plane. The magnetic field lines 852 disposed at a centerline of the magnet 512 are straight and vertical, representing a zero degree (0°) magnetic field orientation of the magnetic flux along the centerline of the magnet 512. The magnetic field lines 850 are curved, such as into ellipses or circles that are tangent to the magnetic field line 852. The curvature of the magnetic field lines 850 changes according to the distance from the zero degree (0°) line 852.

The Y-sensor 514y can be aligned with the 0° magnetic field line 852 at the centerline of the magnet 512. That is, the Y-sensor 514y can be configured to have the 0° magnetic field line 852 as its alignment reference point, and as such, the Y-sensor 514y measures field angles with reference from the 0° magnetic field line 852. While the Y-sensor 514y is in head-to-head alignment with the 0° magnetic field line 852, the Y-sensor 514y detects a magnetic field angle of 0° (i.e., the reference field angle) and outputs a signal having a voltage that corresponds to the 0° field angle in the linear range of the calibration curve of the Y-sensor 514y. Head-to-head alignment of the Y-sensor 514y corresponds to both (1) the 0° reference field angle measured at the alignment reference point, and (2) the output voltage corresponding to the 0° field angle.

While the Y-sensor 514x is in head-to-head alignment with the 0° magnetic field line 852, any movement of the Y-sensor 514y in the Z-Direction would cause the Y-sensor 514x to generate an output voltage corresponding to the 0° field angle of the line 720 that is parallel with the magnetic field line 852. That is, the orientation of the magnetic field emanating from the centerline of the magnet 512 is 0° and does not vary in the Z-Direction (as shown by the straight magnetic field line 852). By aligning the Y-sensor 514x at a location (i.e., at the centerline of the magnet) where the movement in the Z-Direction yields a constant 0° field angle, the Y-sensor 514y becomes insensitive to Z displacement.

As described above, within the defined displacement range within which differences in the shape of the magnetic field are negligible, any lateral cross-section of the magnet 512 in the YZ plane would yield magnetic field lines 850, 852 that have substantially the same field angle produced at the side face of the magnet 512. Accordingly, the Y-sensor 514y becomes insensitive to X displacement by aligning the Y-sensor 514y at a location (i.e., at the centerline of the magnet) where any movement of the Y-sensor 514y in the X-Direction (i.e., the direction into/out-of the page) would yield substantially the same output from the Y-sensor 514y as prior to the movement in the Z-Direction.

The Y-sensor 514y is fixed to the PCB in a position wherein the Y-sensor is sensitive only to movement in the lateral Y-Direction. That is, Y-sensor 514y is disposed where movement in the Z-Direction causes the generation of a 0° field angle before and after the movement. However, any movement of the Y-sensor 514y in the Y-Direction causes the Y-sensor 514y to measure a field angle different from the 0° alignment with the magnetic field line 852, indicating movement of the scanning sensor heads 410a-410b a linear distance away from head-to-head alignment in the Y-Direction.

Embodiments of this disclosure are not limited to having the 0° magnetic field line 852 as the alignment reference point of the Y-sensor 514y. In certain embodiments, such as shown in FIG. 8, the Y-sensor 514y can be configured to have the line 806 as its alignment reference point in order to mid-range the sensor by aligning the sensor with the field angle that corresponds to a combination of the gap separation in the Z-Direction and in the displacement in the Y-Direction when the upper and lower sensor heads are in head-to-head alignment. That is, the upper and lower sensor heads 410a-410b are in head-to-head alignment when the Y-sensor 514y outputs the field angle corresponding to the tangent line 806 (i.e., the reference field angle). More particularly, the Y-sensor 514y is disposed at a position offset from the 0° magnetic flux at the centerline of the magnet 512 in the Y-Direction, where the magnetic field has an orientation tangent to line 806. In this case, leftward movement of the Y-sensor 514y in the Y-Direction causes the Y-sensor to detect a magnetic field orientation having tangent line 802, while rightward movement of the Y-sensor 514y in the Y-Direction causes the Y-sensor to detect a magnetic field orientation having tangent line 808. When the scanning sensor head 410b move further leftward from the line 802, the Y-sensor may detect a magnetic field orientation having tangent line 804. A controller determines the Y-direction displacement based on the Y-Direction linear distance between alignment reference point and the position where a current field angle is measured.

Figure 9:
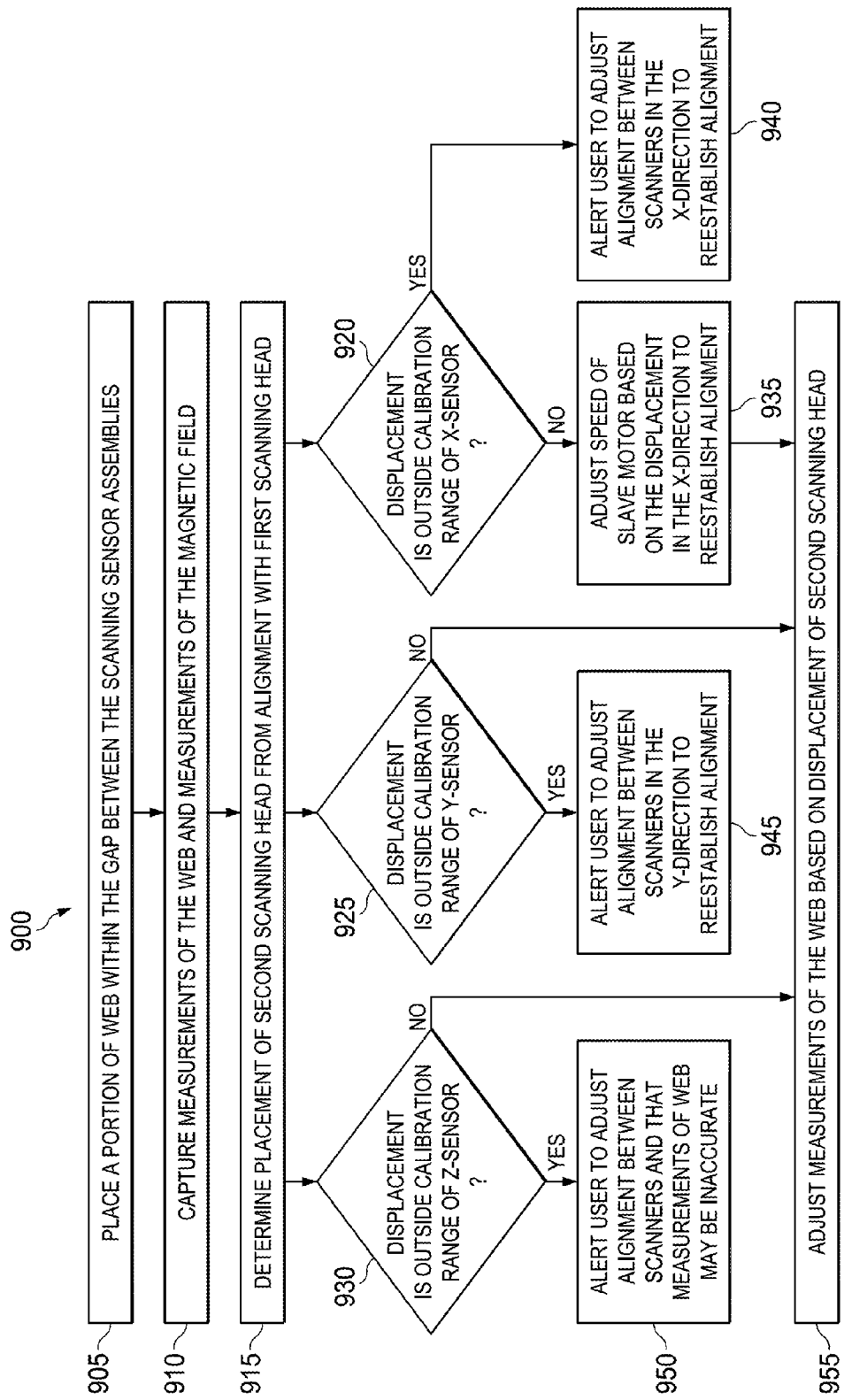
FIG. 9 illustrates an example method for maintaining head-to-head alignment in three primary directions for scanning sensor heads.

FIG. 9 illustrates an example method for maintaining head-to-head alignment in three primary directions for scanning sensor heads. The embodiment of the method 900 shown in FIG. 9 is for illustration only. The method includes operation blocks 905-955 implemented by a web-making or web-processing system, such as the systems 100 and 400. Other embodiments could be used without departing from the scope of this disclosure.

In block 905, a portion of the web 102 is placed between the scanning sensor assemblies 108-110 within the gap between the scanning sensor heads 210a-210b. For example, the pairs of rollers 104a-104b and 106a-106b pull the web 102 into the gap, thereby providing the web sensors 212a-212b access to the web 102. In order to capture measurements of another portion of the web 102, the pairs of rollers 104a-104b and 106a-106b can roll to place a subsequent portion of the web 102 within the gap.

In block 910, the web sensors 212a-212b capture measurements of the web 102 used to identify characteristics of the web 102. At the same time, the position sensor elements 214a-214b capture measurements of the magnetic field. Specifically, the sensor heads 210a-210b move across the web 102 enabling the web sensors 212a-212b and position sensor elements 214a-214b to capture measurements. The motor controllers 308a-308b drive the motors 206a-206b to move the carriages 204a-204b in a lateral cross direction (X-Direction) across the width of the web 102. The sensor heads 210a-210b move together, such as in unison, with the carriages 204a-204b.

In block 915, a controller (e.g., controller 216, 306a-306b, 308a-308b) determines the displacement of the second scanning sensor head 210b from head-to-head alignment with the first scanning sensor head 210a in one or more directions (for example, the cross direction (X-Direction)). Specifically, the controller determines a displacement for each of the one or more directions. For example, the controller can receive a field angle measured in block 910 by the magnetic field orientation sensor 314a or X-sensor 514x, and perform calculations using the measured field angles to determine the lateral cross direction (X-Direction) displacement between the scanning sensor heads 210a-210b. In a similar manner, the controller can receive field angles from the Y-sensor or Z-sensor to determine the lateral machine direction displacement or gap separation, respectively. If there is a misalignment that is too large in any direction, as indicated by a displacement outside the calibration range of a corresponding magnetic field orientation sensor, then the measurements captured by the web sensors 212a-212b may be inaccurate and may mischaracterize the current portion of the web 102. Note that in certain embodiments, the calibration range can be up to 8 mm, yet needs to only include the tolerance distance corresponding to the specified nominal target gap separation.

After block 915, the process 900 moves to blocks 920, 925, and 930, where the controller determines whether the second scanning sensor head 210b is in head-to-head alignment with the first scanning sensor head 210a. In blocks 920, 925, and 930, the controller determines whether the respective lateral cross (X-direction) displacement, lateral machine (Y-direction) displacement, and gap separation (Z-direction) displacement is outside a calibration range of the magnetic field orientation sensor corresponding to the direction. To make this determination, the controller uses each of the displacements determined in block 915. That is, in block 920, in response to receiving the lateral cross (X-direction) displacement of block 915, the controller compares the calibration range of the X-sensor to the received lateral cross displacement. In blocks 925 and 930, the controller makes a similar comparison for the respective Y-sensor and Z-sensor. In block 920, in response to a determination that the displacement is within the calibration range of the X-sensor 514x (shown by an arrow labeled NO), the process 900 moves to block 935. In blocks 925 and 930, in response to a determination that the displacement is within the calibration range of the magnetic field orientation sensor (shown by an arrow labeled NO), the process 900 moves to block 955.

In block 935, when the controller determines that the lateral cross displacement is within the calibration range of the X-sensor (shown by an arrow labeled YES), the motor controller 308b adjusts the speed of the motor 206b to reestablish head-to-head alignment. For example, if the second scanning sensor head 210b lags behind the first sensor head 210a, the slave motor controller 308b could output a PMS to increase the speed of the motor 206b until proper alignment is reached, then readjust the speed of the motor 206b to match the speed of the motor 206a. Adjustments to the displacement in the X-Direction are output to the controller, and the process 900 moves to block 955 where the adjusted X-Direction displacement is used to adjust measurements of the web.

In block 940, when the controller determines that the lateral machine displacement is outside the calibration range of the X-sensor, the motor controller 308b alerts a user/technician, such as by generating an alarm. In block 940, the controller implements a similar process as implemented in block 945 (described more particularly below), but corresponds to the X-direction and X-sensor instead of the Y-direction and Y-sensor. In response to a determination that the field angle measured by the X-sensor is re-established to be within the calibration range of the X-sensor, the process 900 moves to block 955.

In block 945, when the controller determines that the lateral machine displacement is outside the calibration range of the Y-sensor, the motor controller 308b alerts a user/technician, such as by generating an alarm. For example, if the second scanning sensor head 210b is disposed too far from the first sensor head 210a in a positive Y-direction, the alarm could indicate to the user/technician an adjustment amount by which to move the second scanning sensor head 210b in a negative Y-direction to reestablish head-to-head alignment. Alternatively, the alarm could indicate to move the first sensor head 210a in the positive Y-direction to reduce the displacement and reestablish head-to-head alignment. The alarm could indicate that measurements of the web, as measured by the web sensors 212a-212b, may be inaccurate or that characterizations of the web may be misidentified. In response to a determination that the field angle measured by the Y-sensor is within the calibration range of the Y-sensor, the process 900 moves to block 955.

In block 950, when the controller determines that the gap separation (Z-direction displacement) is outside the calibration range of the Z-sensor, the motor controller 308b alerts a user/technician, such as by generating an alarm. In block 950, the controller implements a similar process as implemented in block 945, but corresponds to the Z-direction and Z-sensor instead of the Y-direction and Y-sensor. In response to a determination that the field angle measured by the Z-sensor is within the calibration range of the Z-sensor, the process 900 moves to block 955.

In block 955, the controller adjusts the measurements of the web 102 based on the displacement of the second scanning sensor head 210b from the first scanning sensor head 210a.

In the above description, the directions being measured are defined as X (cross direction), Y (machine direction), and Z (gap). Note, however, that any other suitable directions could be measured using the approach described in this patent document. For example, this approach could be used to capture measurements in any three orthogonal directions, regardless of whether those orthogonal directions align with the cross direction, machine direction, and gap.

Although FIGS. 1 through 9 illustrate examples of a web-making or web-processing system and related details, various changes may be made to FIGS. 1 through 9. For example, the functional division shown in FIGS. 1-8 is for illustration only. Various components in FIGS. 1-8 could be combined, further subdivided, or omitted and additional components could be added according to particular needs. In addition, while FIG. 9 illustrates a series of steps, various steps in each figure could overlap, occur in parallel, or occur any number of times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
generating a magnetic field;
capturing, by multiple magnetic field orientation sensors, measurements of the magnetic field by:
  measuring, by a first magnetic field orientation sensor, a field angle of the magnetic field in a first direction with reference to a reference field angle, wherein the first magnetic field orientation sensor is disposed substantially in alignment with a centerline of the magnetic field; and
  measuring, by a second magnetic field orientation sensor, a field angle of the magnetic field in a plane defined by the first direction and a second direction, the first and second directions orthogonal to each other, wherein the second magnetic field orientation sensor is disposed offset from the centerline of the magnetic field such that an output from the second magnetic field orientation sensor represents a combination of (i) a displacement of first and second scanning sensor heads in the first direction and (ii) a gap separation of the first and second scanning sensor heads in the second direction; and
identifying, using the measurements of the magnetic field, (i) the displacement of the first and second scanning sensor heads in the first direction and (ii) the gap separation of the first and second scanning sensor heads in the second direction.

2. A method comprising:
generating a magnetic field;
capturing, by multiple magnetic field orientation sensors, measurements of the magnetic field; and
identifying, using the measurements of the magnetic field, (i) a displacement of first and second scanning sensor heads in a first direction and (ii) a gap separation of the first and second scanning sensor heads in a second direction;
wherein:
  at least one of the magnetic field orientation sensors is disposed offset from a centerline of the magnetic field such that an output from the at least one magnetic field orientation sensor represents a combination of the displacement and the gap separation;
  each of the magnetic field orientation sensors is calibrated to operate within a calibration range in which a voltage output from the magnetic field orientation sensor is related to a field angle measurement of the magnetic field;

within the calibration range, the field angle measurement of the magnetic field accurately represents a linear distance from an alignment reference point;

at limit points of the calibration range, (i) a minimum field angle measurement accurately represents a first linear distance from the alignment reference point and (ii) a maximum field angle measurement accurately represents a second linear distance from the alignment reference point in an opposite direction; and a tolerance corresponding to a specified nominal target gap separation is disposed between the limit points of the calibration range.

3. The method of claim 1, wherein the first and second magnetic field orientation sensors are disposed in a common plane or in parallel planes.

4. The method of claim 1, further comprising:
moving the first and second scanning sensor heads across a surface of a web of material and;
capturing measurements associated with the web.

5. The method of claim 4, further comprising:
adjusting the measurements associated with the web based on at least one of:
 the displacement of the first and second scanning sensor heads in the first direction; and
 the gap separation of the first and second scanning sensor heads in the second direction.

6. A multiple-sensor assembly comprising:
multiple magnetic field orientation sensors configured to capture measurements of a magnetic field in order to identify (i) a displacement of first and second scanning sensor heads in a first direction and (ii) a gap separation of the first and second scanning sensor heads in a second direction, the magnetic field orientation sensors comprising:
 a first magnetic field orientation sensor configured to measure a field angle of the magnetic field in the first direction with reference to a reference field angle, wherein the first magnetic field orientation sensor is disposed substantially in alignment with a centerline of the magnetic field; and
 a second magnetic field orientation sensor configured to measure a field angle of the magnetic field in a plane defined by the first and second directions, the first and second directions orthogonal to each other, wherein the second magnetic field orientation sensor is disposed offset from the centerline of the magnetic field such that an output from the second magnetic field orientation sensor represents a combination of the displacement and the gap separation.

7. A multiple-sensor assembly comprising:
multiple magnetic field orientation sensors configured to capture measurements of a magnetic field in order to identify (i) a displacement of first and second scanning sensor heads in a first direction and (ii) a gap separation of the first and second scanning sensor heads in a second direction;
wherein:
 at least one of the magnetic field orientation sensors is disposed offset from a centerline of the magnetic field such that an output from the at least one magnetic field orientation sensor represents a combination of the displacement and the gap separation;

each of the magnetic field orientation sensors is calibrated to operate within a calibration range in which a voltage output from the magnetic field orientation sensor is related to a field angle measurement of the magnetic field;

within the calibration range, the field angle measurement of the magnetic field accurately represents a linear distance from an alignment reference point;

at limit points of the calibration range, (i) a minimum field angle measurement accurately represents a first linear distance from the alignment reference point and (ii) a maximum field angle measurement accurately represents a second linear distance from the alignment reference point in an opposite direction; and a tolerance corresponding to a specified nominal target gap separation is disposed between the limit points of the calibration range.

8. The multiple-sensor assembly of claim 6, wherein the first and second magnetic field orientation sensors are disposed in a common plane or in parallel planes.

9. The multiple-sensor assembly of claim 8, wherein the magnetic field orientation sensors further comprise:
a third magnetic field orientation sensor configured to measure a field angle of the magnetic field in a third direction in order to identify a displacement of the first and second scanning sensor heads in a third direction;
wherein the third magnetic field orientation sensor is disposed in a plane that is orthogonal to the common plane or to the parallel planes.

10. A system comprising:
first and second scanning sensor heads each configured to move across a surface of a web of material and capture measurements associated with the web, wherein:
 the first scanning sensor head includes a magnet configured to generate a magnetic field; and
 the second scanning sensor head includes multiple magnetic field orientation sensors configured to capture measurements of the magnetic field in order to identify (i) a displacement of the first and second scanning sensor heads in a first direction and (ii) a gap separation of the first and second scanning sensor heads in a second direction, the magnetic field orientation sensors comprising:
  a first magnetic field orientation sensor configured to measure a field angle of the magnetic field in the first direction with reference to a reference field angle, wherein the first magnetic field orientation sensor is disposed substantially in alignment with a centerline of the magnetic field; and
  a second magnetic field orientation sensor configured to measure a field angle of the magnetic field in a plane defined by the first and second directions, the first and second directions orthogonal to each other, wherein the second magnetic field orientation sensor is disposed offset from the centerline of the magnetic field such that an output from the second magnetic field orientation sensor represents a combination of the displacement and the gap separation.

11. A system comprising:
first and second scanning sensor heads each configured to move across a surface of a web of material and capture measurements associated with the web;
wherein:
 the first scanning sensor head includes a magnet configured to generate a magnetic field;

the second scanning sensor head includes multiple magnetic field orientation sensors configured to capture measurements of the magnetic field in order to identify (i) a displacement of the first and second scanning sensor heads in a first direction and (ii) a gap separation of the first and second scanning sensor heads in a second direction;

at least one of the magnetic field orientation sensors is disposed offset from a centerline of the magnetic field such that an output from the at least one magnetic field orientation sensor represents a combination of the displacement and the gap separation;

each of the magnetic field orientation sensors is calibrated to operate within a calibration range in which a voltage output from the magnetic field orientation sensor is related to a field angle measurement of the magnetic field;

within the calibration range, the field angle measurement of the magnetic field accurately represents a linear distance from an alignment reference point;

at limit points of the calibration range, (i) a minimum field angle measurement accurately represents a first linear distance from the alignment reference point and (ii) a maximum field angle measurement accurately represents a second linear distance from the alignment reference point in an opposite direction; and a tolerance corresponding to a specified nominal target gap separation is disposed between the limit points of the calibration range.

12. The system of claim 10, wherein the first and second magnetic field orientation sensors are disposed in a common plane or in parallel planes.

13. The system of claim 10, further comprising:
processing circuitry configured to identify, using the measurements of the magnetic field, the displacement and the gap separation.

14. The system of claim 13, wherein the processing circuitry is further configured to adjust the measurements associated with the web based on at least one of:
the displacement of the first and second scanning sensor heads in the first direction; and
the gap separation of the first and second scanning sensor heads in the second direction.

15. The system of claim 10, wherein:
each of the magnetic field orientation sensors is calibrated to operate within a calibration range in which a voltage output from the magnetic field orientation sensor is related to the associated field angle measurement of the magnetic field;
within the calibration range, the field angle measurement of the magnetic field accurately represents a linear distance from an alignment reference point;
at limit points of the calibration range, (i) a minimum field angle measurement accurately represents a first linear distance from the alignment reference point and (ii) a maximum field angle measurement accurately represents a second linear distance from the alignment reference point in an opposite direction; and
a tolerance corresponding to a specified nominal target gap separation is disposed between the limit points of the calibration range.

16. The system of claim 11, wherein the magnetic field orientation sensors comprise:
a first magnetic field orientation sensor configured to measure a field angle of the magnetic field in the first direction with reference to a reference field angle, wherein the first magnetic field orientation sensor is disposed substantially in alignment with the centerline of the magnetic field; and
a second magnetic field orientation sensor configured to measure a field angle of the magnetic field in a plane defined by the first and second directions, wherein the second magnetic field orientation sensor is disposed offset from the centerline of the magnetic field.

17. The method of claim 1, wherein:
each of the magnetic field orientation sensors is calibrated to operate within a calibration range in which a voltage output from the magnetic field orientation sensor is related to the associated field angle measurement of the magnetic field;
within the calibration range, the field angle measurement of the magnetic field accurately represents a linear distance from an alignment reference point;
at limit points of the calibration range, (i) a minimum field angle measurement accurately represents a first linear distance from the alignment reference point and (ii) a maximum field angle measurement accurately represents a second linear distance from the alignment reference point in an opposite direction; and
a tolerance corresponding to a specified nominal target gap separation is disposed between the limit points of the calibration range.

18. The method of claim 2, wherein capturing the measurements of the magnetic field comprises:
measuring, by a first magnetic field orientation sensor, a field angle of the magnetic field in the first direction with reference to a reference field angle, wherein the first magnetic field orientation sensor is disposed substantially in alignment with the centerline of the magnetic field; and
measuring, by a second magnetic field orientation sensor, a field angle of the magnetic field in a plane defined by the first and second directions, wherein the second magnetic field orientation sensor is disposed offset from the centerline of the magnetic field.

19. The multiple-sensor assembly of claim 6, wherein:
each of the magnetic field orientation sensors is calibrated to operate within a calibration range in which a voltage output from the magnetic field orientation sensor is related to the associated field angle measurement of the magnetic field;
within the calibration range, the field angle measurement of the magnetic field accurately represents a linear distance from an alignment reference point;
at limit points of the calibration range, (i) a minimum field angle measurement accurately represents a first linear distance from the alignment reference point and (ii) a maximum field angle measurement accurately represents a second linear distance from the alignment reference point in an opposite direction; and
a tolerance corresponding to a specified nominal target gap separation is disposed between the limit points of the calibration range.

20. The multiple-sensor assembly of claim 7, wherein the magnetic field orientation sensors comprise:
a first magnetic field orientation sensor configured to measure a field angle of the magnetic field in the first direction with reference to a reference field angle, wherein the first magnetic field orientation sensor is disposed substantially in alignment with the centerline of the magnetic field; and
a second magnetic field orientation sensor configured to measure a field angle of the magnetic field in a plane defined by the first and second directions, wherein the second magnetic field orientation sensor is disposed offset from the centerline of the magnetic field.

\* \* \* \* \*